United States Patent [19]

Putz

[11] Patent Number: 5,097,835
[45] Date of Patent: Mar. 24, 1992

[54] SUBDURAL ELECTRODE WITH IMPROVED LEAD CONNECTION

[75] Inventor: David A. Putz, Racine, Wis.

[73] Assignee: Ad-Tech Medical Instrument Corporation, Racine, Wis.

[21] Appl. No.: 506,271

[22] Filed: Apr. 9, 1990

[51] Int. Cl.$^5$ .......................................... A61B 5/0478
[52] U.S. Cl. .................................................... 128/642
[58] Field of Search ............... 128/642, 639, 640, 644, 128/784, 785, 798, 802

[56] References Cited

U.S. PATENT DOCUMENTS

| | | | |
|---|---|---|---|
| 3,547,104 | 12/1970 | Buffington | 128/640 X |
| 4,050,453 | 9/1977 | Castillo et al. | 128/640 |
| 4,319,579 | 3/1982 | Cartnell | 128/640 |
| 4,516,820 | 5/1985 | Kuzma | 339/48 |
| 4,735,208 | 4/1988 | Wyler et al. | 128/642 |
| 4,771,783 | 9/1988 | Roberts | 128/640 |
| 4,774,371 | 5/1988 | Harris | 128/786 |

Primary Examiner—Lee S. Cohen
Attorney, Agent, or Firm—Peter N. Jansson, Ltd.

[57] ABSTRACT

The improved subdural electrode for determining epileptogenic foci is of the type having two dielectric layers. The electrode includes at least one electrical lead wire having a portion of its length interposed between the dielectric layers. At least one electrode disk is interposed between the layers and has a tab formed thereon. Connection of the tab and the lead wire is by folding the outer segment of the tab toward its inward segment to crimp the wire between them. An electrically conductive circuit between the wire and the tab is thereby created. The electrical and mechanical integrity of the connection is improved by wrapping the wire about the tab several times before crimping. The connection is also improved by positioning the wrapped wire, prior to final crimping, adjacent the fold defined between the outer and inward segments.

19 Claims, 3 Drawing Sheets

SUBDURAL ELECTRODE WITH IMPROVED LEAD CONNECTION

FIELD OF THE INVENTION

This invention is related generally to electrodes for monitoring cortical electrical activity in order to define cortical epileptogenic foci and, more particularly, to such an electrode having improved means for attaching together the disks and electrical lead wires used therein.

BACKGROUND OF THE INVENTION

Surgical removal of epileptogenic brain tissue is indicated for treatment of many medically refractory focal seizure disorders, epilepsy being by far the most common. One of the important factors in providing good results from such surgery is the degree of accuracy in identifying epileptogenic foci. Various approaches have been used in attempting to determine epileptogenic foci, one of them being the employment of subdural electrodes. Of course, all such approaches involve sensing of cortical electrical activity using electrical contacts or disks as parts of electrodes applied in various ways.

Intracranial surgery for the treatment of epilepsy was undertaken at least as early as about 1927. Such surgery is known to have involved the use of some sort of electrode in some way. Subdural electrodes have been used to help identify epileptogenic foci since at least as early as 1954. Stated another way, neurosurgeons have had a concern about the mechanical and electrical integrity of subdural electrodes—and especially about the integrity of connections within the electrode itself—for more than 35 years.

Intracranial recording techniques have used either of two different types of electrodes—intracortical depth electrodes or subdural electrodes. The relative safety of subdural electrodes is due to the fact that, unlike depth electrodes, they are not invasive of brain tissue. Depth electrodes are narrow, typically cylindrical dielectric structures which are inserted into the brain in order to establish good electrical contact with different portions of the rain. On the other hand, subdural electrodes are flat strips which support contacts or disks spaced thereon. An earlier type of such electrode used as an electrical contact a small metallic ball formed on the end of a lead wire.

Subdural electrodes are inserted between the dura and the brain, along the surface of and in contact with the brain, but not within the brain. Insertion is by incising the patient's scalp and spreading it with retractors, drilling a burr hole in the skull and incising the dura across the diameter of the burr hole. Tack-up sutures are placed in both dural margins for retraction and the electrode grasped with forceps and inserted under the dural edge, all in a known manner. Typically, four electrodes are used per burr hole and four burr holes in the patient's skull are used for more accurate location of the foci.

The lead wires for all electrodes are brought to the exterior and following temporary sutured closure of the dura and the scalp, cortical electrical activity is monitored. Typically, such monitoring occurs over a period of one to three weeks. At the end of the monitoring period, the electrodes are, of course, removed. With the exception of electrodes made in accordance with U.S. Pat. No. 4,735,208, such removal often requires major general surgery in the operating room, using a general anesthetic. This is not only expensive but it is also very difficult for the patient.

Also of the foregoing activity (and the anticipation of the procedure) can be very traumatizing to the patient, both physically and phychologically. The psychological effect may be rather profound, notwithstanding the relative safety of the procedure. Clearly, any inventive advancement which not only facilitates successful treatment of certain seizure disorders (which are sometimes a source of acute embarrassment to the patient) but which also helps avoid unnecessary major surgery would be welcomed by patient and physician alike.

Subdural electrodes occur in at least two embodiments, namely strip electrodes and grid electrodes. A strip electrode is shown in U.S. Pat. No. 4,735,208 and such electrodes use upper and lower elongated flexible dielectric layers to form the strip. Confined between the layers is a plurality of spaced, aligned flat contact disks together with their electrical lead wires.

Subdural grid electrodes use an array of spaced flat disks similarly confined between two dielectric layers. An example of such a grid electrode is shown in U.S. Pat. No. 4,869,255. The aforementioned patents are assigned to the same assignee as this invention and are incorporated herein by reference.

Irrespective of whether a subdural electrode is of the strip or grid type, such electrodes include an imperforate upper dielectric layer which is that layer which contacts the dura tissue. Such electrodes also have a lower dielectric layer which is in direct contact with the brain when the electrode has been inserted between the brain and the surrounding dura tissue. This lower layer has at least one and preferably a plurality of openings therethrough. A plurality of electrode disks is interposed and confined between the layers, there being one disk for each opening in the lower dielectric layer. Each disk is positioned adjacent its associated opening and is connected to a separate, dedicated electrical lead wire.

Typically, such lead wires have a bare portion which is connected to the disk and an insulated portion which extends from the disk to an exit point on the electrode for connection to a diagnostic instrument. Such disks and lead wires are typically extremely small. For example, preferred disks have a diameter in the range of 0.100 inches to 0.250 inches with a highly preferred diameter being 0.156 inches. The associated lead wires preferably range in size from 36 gauge to 50 gauge and a highly preferred wire size is 40 gauge. Such 40 gauge wire has a diameter of about 0.004", only slightly larger than that of a human hair. Such disks and lead wires are commonly made of stainless steel, platinum or other metals suitable for cranial implantation.

Various means for making electrical connections have been used in other environments. Soldering is one such approach but is not practical for intracranial electrodes since parts to be soldered (disks and wires) must have flux applied thereto. Flux residue must be thoroughly removed before the parts are used and there is always some change of incomplete cleaning. Stated another way, the use of flux risks the introduction of chemical contaminants into the cranial cavity.

Another approach to making electrical connections generally involves the use of recently-introduced conductive adhesives. However, such adhesives often contain silver which has a tendency to introduce a level of toxicity in intracranial applications.

Heretofore, connection of a disk and its lead wire has been by welding, such delicate welding being accomplished by the careful application of heat from an external source. Attachment by welding apparently tends to cause certain changes in the molecular structure of the metal at the site of the weld. Specifically, such molecular structure changes seem to impart a degree of brittleness to that short length of lead wire which is connected to a given disk. The result is that a phenomenon in the nature of a "boundary" is formed between the more brittle end of the wire connected to the disk and the more ductile remainder of the wire strand which leads from the disk.

Such apparent change in molecular structure and the formation of any boundary tends to make the lead wire more susceptible to breakage at the point at which the wire connects to the disk. Breakage is undesirable for several reasons. Among the most important is the resulting inability to derive an electrical signal from a particular disk. The absence of a particular signal will either impair the accuracy of the resulting diagnosis or, assuming the breakage is detected, will require removal of the defective electrode. As explained below, electrode replacement cannot occur for some time following such an event.

In addition, breakage of the electrical lead wire may have a tendency to permit the disk to migrate from the electrode. In such a case, there is a change that the loss of a disk would go undetected. Clearly, the presence of such foreign matter would be adverse to the welfare of the patient.

It is apparent that subdural electrodes perform their function by permitting the detection and analysis of electrical signals. Such signals are produced by electrical currents that are extremely minute. Therefore, even if breakage of an electrical lead does not occur (and such breakage is relatively rare), slight variations in electrical resistances at the points of welding may have a tendency to distort or otherwise impair the electrical signals emanating from the electrode. Therefore, the quality of the signals—and of the diagnosis and any resulting brain surgery based upon them—may be impaired.

An understanding of the effect of a failure of a connection between a disk and its lead wire is particularly important. In the event of such failure, the electrode is unusable and must be removed. Further, a new electrode cannot be re-inserted for a period of several months, perhaps up to a year. This is so since such repeated insertions which are too closely spaced in time tend to result in scarring of the very delicate cortex tissue. In fact, some researchers believe that such scarring itself may cause or contribute to seizures.

Since a good diagnosis of foci cannot proceed in the absence of even one electrode and since immediate re-insertion is not advised, all electrodes must be removed from all burr holes. Then the dura, skull and scalp openings must be closed and further diagnostic effort delayed for an extended period. One can only imagine the level of discouragement and anxiety which may result in a patient who experiences such an aborted diagnostic attempt and subsequent delay.

A subdural electrode which has disks and lead wires attached to one another using means other than the application of heat and where the means of attachment enhances the electrical and mechanical integrity of the connection would be an important advance in the art.

OBJECTS OF THE INVENTION

It is an object of this invention to overcome some of the problems and shortcomings of the prior art.

Another object of this invention is to provide a subdural electrode using electrode disks, each of which has a tab for use in connecting an electrical lead wire thereto.

Another object of this invention is to provide a subdural electrode wherein the tab is connected to the bare portion of an electrical lead wire by crimping.

Still another object of this invention is to provide a subdural electrode wherein the bare portion of the lead wire is wrapped about the tab to provide better electrical contact and mechanical strength.

Another object of this invention is to provide a subdural electrode wherein each electrode disk used there has an inward segment and an outer segment and the outer segment is folded toward the inward segment to clamp the bare portion of the lead wire therebetween, thereby providing a relatively flat connection site.

Yet another object of this invention is to provide an improved electrode wherein the outer segment lies adjacent the upper dielectric layer of the electrode after the electrical lead wire has been clamped, thereby providing a relatively smooth lower dielectric layer to be in contact with the brain.

Another object of this invention is to provide an improved electrode wherein the disks and electrical lead wires are connected to one another by means which avoid the application of heat in making the connection.

Still another object of this invention is to provide an improved electrode which is unaffected by the presence of magnetic resonance imaging.

These and other important objects will be apparent from the descriptions of this invention which follow.

SUMMARY OF THE INVENTION

In general, an improved subdural electrode for determining epileptogenic foci is of the type having two dielectric layers. The electrode includes at least one electrical lead wire having a portion of its length interposed between the dielectric layers. At least one electrode disk is interposed between the layers and has a tab formed thereon. Connection of the tab and the lead wire is by crimping the tab to the wire to create an electrically conductive circuit between them. The lead wire is connected to a diagnostic instrument and the electrode used to detect and interpret minute electrical signals. These signals assist the surgeon in locating and removing epileoptogenic tissue.

In a highly preferred embodiment, the tab has an inward segment attached to and extending from the disk. An outer segment is attached to and extends from the inward segment and the tab is crimped to the wire by folding the outer segment toward the inward segment, thereby clamping the wire between the segments. Improved electrical contact and mechanical strength of the tab-wire connection are achieved by wrapping the wire about the tab several times before crimping. When the outer segment is folded toward the inward segment, a fold is defined. A preferred location for the bare portion of the wire is between the folded, clamped segments and immediately adjacent the fold.

In preferred subdural electrodes, the lower dielectric layer, that which is in contact with the brain when the electrode is in use, is made as smooth as possible. To help maintain such smoothness, the direction of folding of the outer segment toward the inward segment is preferably such that the outer segment lies adjacent the upper dielectric layer.

When the electrode is finally assembled, it is preferred that the sharp end of the bare portion of the wire either not exposed or if exposed, be positioned to be confined and "captured" by the upper dielectric layer. One way in which this is done is to wrap the bare portion of the lead wire about the tab in such way as to confine the sharp wire end within the "envelope" defined by the outer segment and the inward segment when they are crimped together. A second approach is to position the exposed end atop the disk, i.e., between the disk and the upper layer and immediately adjacent the upper layer.

Further details regarding the invention are set forth in the following detailed description.

DETAILED DESCRIPTION OF PREFERRED EMBODIMENTS

The figures show the improved subdural electrode 10 in accordance with the invention.

Figure 1:
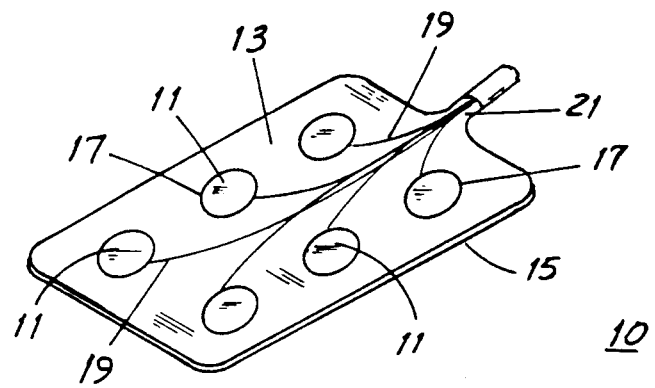
FIG. 1 is a perspective view, greatly enlarged, of a subdural electrode of the grid type.

FIG. 1 shows a subdural electrode 10 of the grid type wherein an array of electrode disks 11 is interposed between a lower dielectric layer 13 and an upper dielectric layer 15. The lower layer 13 has a plurality of openings 17 through it for exposing an electrode disk 11 at each opening 17. Each disk 11 is connected to a separate electrical lead wire 19 in a manner described below. The lead wires 19 are brought to a common exit point 21 on the electrode 10, thereby facilitating connection of each disk 11 of an electrode 10 to a diagnostic instrument.

Figure 2:
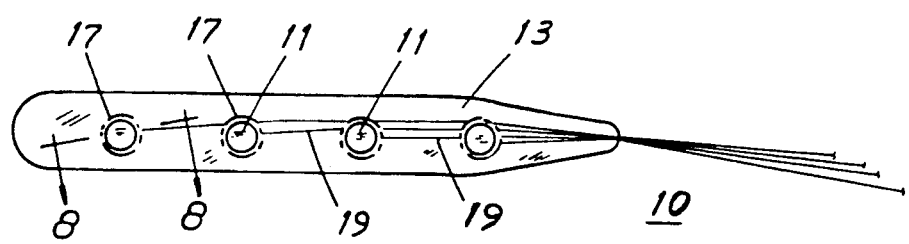
FIG. 2 is a bottom plan view, greatly enlarged, of a subdural electrode of the strip type.

FIG. 2 shows a subdural electrode 10 of the strip type wherein at least one and preferably a plurality of electrode disks 11 is interposed and confined between a lower dielectric layer 13 and an upper dielectric layer (not shown). Like the layer 13 of FIG. 1, the lower dielectric layer 13 has a plurality of openings 17 formed in it for exposing an electrode disk 11 at each opening 17. Similarly, each disk 11 is connected to a separate electrical lead wire 19 in the manner described below.

Figure 8:
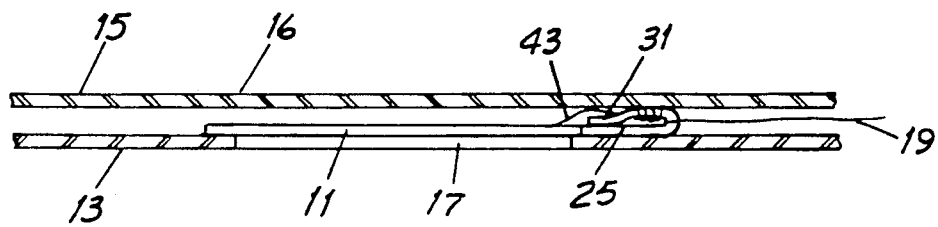
FIG. 8 is an elevation view, greatly enlarged and with parts shown in cross section and other parts broken away, of a portion of the electrode of FIG. 2, taken along the viewing plane 8—8 of FIG. 2, with the electrode components shown in a slightly separated or exploded position, one to another.
Figure 10:
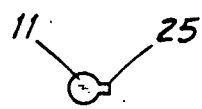
FIG. 10 is a top plan view of an electrode disk, like the disk shown in FIG. 3, shown approximately actual size.

Referring also to FIG. 8 in either the grid electrode 10 or the strip electrode 10, each disk 11 is "captured" between the layers 13 and 15 by the edges 16 of the openings 17 in the lower layer 13. Each opening 17 defines a slightly smaller shape than the shape of the underlying disk 11. Each such edge 16 therefore slightly overlaps the outer perimeter of an associated disk 11. Because such overlap is rather slight, each of the disks 11 has a major portion of its lower surface directly exposed to and in contact with brain tissue. Each disk 11 is therefore able to sense minute electrical signals which are analyzed for locating epileptogenic foci to permit subsequent surgical removal thereof.

Figure 3:
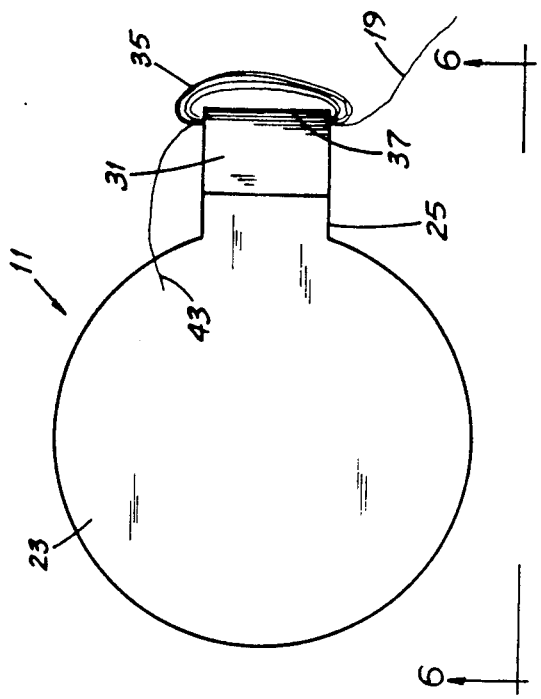
FIG. 3 is a top plan view, greatly enlarged, of an electrode disk.
Figure 4:
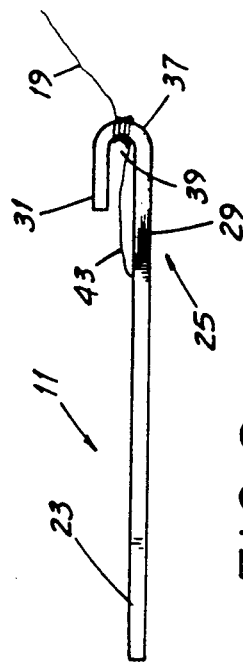
FIG. 4 is a side elevation or edge view of the disk shown in FIG. 3, taken along the viewing plan 4—4 of FIG. 3.

Referring next to FIGS. 3 and 4, a preferred electrode disk 11 is shown to include a planar, generally circular body 23 with a generally rectangular tab 25 extending therefrom. The tab 24 has a longitudinal axis 27 and in a preferred embodiment, the maximum dimension D of the disk 11, as measured generally normal to the longitudinal axis, is at least four times greater than the width W of the tab 25, also measured normal to the axis. A ratio of D to W of about five is common, although such ratio could vary appreciably without departing from the principles of the invention.

In a highly preferred embodiment, the diameter D of the disk 11 is about 0.156 inches, the width W of the tab 25 is about 0.031 inches, the tab 25 has a length of about 0.062 inches and both the disk 11 and the tab 25 have a thickness, as shown in FIG. 4, of about 0.002 inches. While disks (and associated openings) having other shapes may be used, circular disks 11 and openings 17 are commonly used. The use of circular disks 11 avoids corners or other projections which may interfere with the insertion of removal of the electrode.

Figure 5:
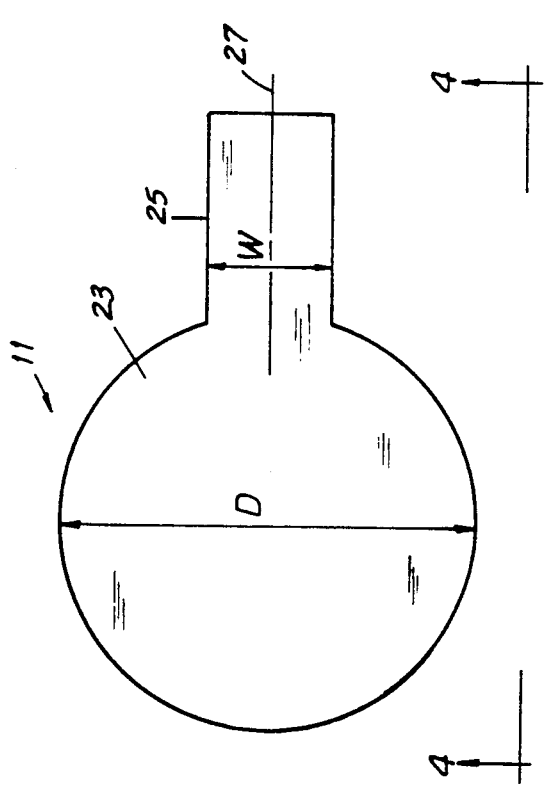
FIG. 5 is a top plan view of the disk of FIG. 3 shown with the electrical lead wire partially connected thereto.
Figure 6:
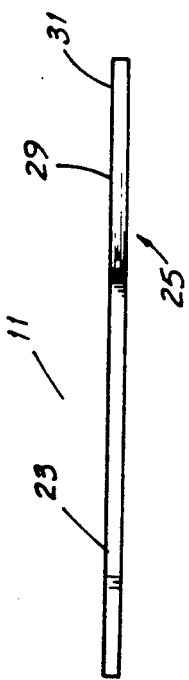
FIG. 6 is a side elevation or edge view of the disk and wire of FIG. 5, taken along the viewing plane 6—6 of FIG. 5.
Figure 7:
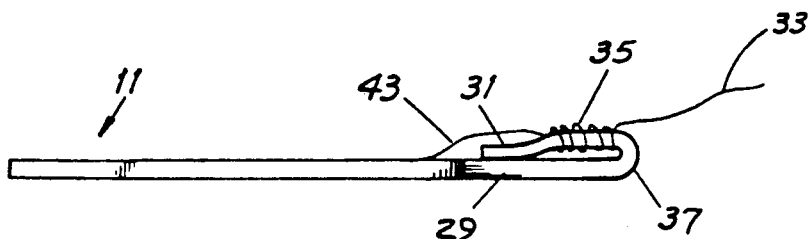
FIG. 7 is a side elevation view similar to that of FIG. 6 except with the disk and electrical lead wire fully connected together.

Referring next to FIGS. 5, 6 and 7 and for purposes of the following explanation, the tab 25 may be considered to have an inward segment 29 which is attached to and extends from the disk 11. An outer segment 31 is attached to and extends from the inward segment 29 and it should be appreciated that the disk 11 and the tab 25 are formed from a single sheet of conductive metal. Preferred metals for cranial implantation are platinum, a nonferrous metal, or stainless steel containing less than about 30% ferrous material.

A preferred electrical lead wire 19 is also formed of stainless steel, platinum or one of other alloys which lend themselves to cranial implantation. One highly preferred wire 19 is sold and 40 gauge. Another preferred wire 19 is made of multiple strands and likewise has about the same diameter. The electrode lead wire 19, whether solid or stranded, includes an extended portion 33 which is covered with a thin dielectric or insulating material and a bare portion 35 from which the insulating material has been removed or to which it has not been applied. As described below, the bare portion 35 is that which is used to make the electrical connection between the lead wire 19 and the disk 11.

To perform the electrical connection, the outer segment 31 is folded toward the inward segment 29 to define a fold 37. Preliminary folding of the outer segment 31 toward the inward segment 29 is only partial and to the degree necessary to define a U-shaped space 39 between the segments 29 and 31. The bare portion 35 of the lead wire 19 is then placed in electrical contact with the tab 25, preferably at a position adjacent the fold 37.

It is possible to make an electrical and mechanical connection between the wire 19 and the tab 25 in one of several ways. One is by placing only a single increment of the bare portion 35 within the U-shaped space 39 or by making a single wrap of the portion 35 about the tab 25 and finally crimping the outer segment 31 to contact the inward segment 29 and clamp the bare portion 35 therebetween. However, it is preferred that the bare portion 35 be wrapped at least three times, and preferably four or five times, about the tab 25 and in intimate contact therewith. Following such wrapping, the tab 25 is crimped to the wire by further folding the outer segment 31 toward the inward segment 29. Folding and crimping are carried out until the segments 29, 31 are each in contact with the several wrapped turns of the bare portion 35 and the bare portion 35 is clamped between the segments 29, 31 as shown in FIG. 8.

Such wrapping and clamping of the bare portion 35 provides a secure mechanical connection between the wire 19 and the tab 25. In addition, multiple turns of the bare portion 35 are in contact with both the outer segment 31 and the inward segment 29 and this enhances the quality of and reduces the resistance of the electrical connection.

Figure 9:
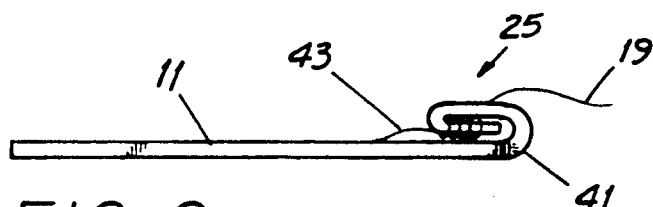
FIG. 9 is a side elevation view of a disk and wire, similar to that of FIG. 6, and showing another embodiment of the improved lead attachment.

Referring to FIGS. 7 and 9, it is preferred that the disk 11 and its connected electrical lead wire 19 are oriented in such way that the folded outer segment 31 lies adjacent the upper dielectric layer 15, rather than the lower dielectric layer 13. This will help assure that the brain-contacting lower dielectric layer 13 is made relatively smooth. In FIGS. 7 and 8, a portion of the outer segment 31 is shown in a slightly spaced relationship to the inward segment 29. Also, the wraps of the bare portion 35 of the lead wire 19 are shown somewhat spaced apart and loosely wrapped. Such depictions help understand how the improved electrode 10 is made. In practice, the wraps of the bare portion 35 would be tightly wound, closely spaced or contacting one another and positioned adjacent the fold 37. Also, the outer segment 31 would be crimped tightly against the inward segment 29 with the bare portion 35 clamped therebetween.

In the second embodiment of the invention as shown in FIG. 9, the crimped tab 25 is folded once again toward the disk 11, such folding being generally at the juncture 41 of the disk 11 and the tab 25. While this arrangement increases the thickness of the electrode 10 somewhat at the location of crimping, it also provides a degree of additional force to help clamp the bare portion 35 and maintain a low resistance, secure electrical and mechanical connection.

It is preferred that the improved subdural electrode 10 be constructed in such a way that when it is finally assembled, the sharp end 43 of the bare portion 35 is either not exposed or if exposed, is positioned to be confined by the upper dielectric layer 15. One approach is to wrap the bare portion 35 of the lead wire 19 about the tab 25 in such a way as to confine the sharp wire end 43 within the "envelope" defined by the outer segment 31 and the inward segment 29 when they are crimped together. A second approach is shown in FIGS. 6, 7, 8 and 9 wherein the exposed end 43 is positioned atop the disk 11, i.e., between the disk 11 and the upper layer 15 and immediately adjacent the upper layer 15.

In operation, either type of electrode 10 is inserted between the brain and the dura tissue using known procedures. Each disk 11 becomes a receptor of minute electrical signals occurring within the brain and useful in certain diagnostic procedures. The improved connection helps assure excellent electrical continuity between the disk 11 and the wire 19 and imparts a high level of mechanical strength of this connection.

Because of the importance of these characteristics, the matter of connection integrity deserves additional emphasis. Since such electrodes 10 are usually left in place within the skull for an extended period of time, continuing connection integrity helps obviate a need for major general surgery (and attendant patient trauma) to remove a defective electrode 10. Further, connections between the disks 11 and their associated wires 19 which are consistently low in resistivity help detected and analyze minute electrical signals in a much more accurate way than may otherwise have been possible. And withdrawal of the electrodes 10, by grasping and pulling on the electrical lead wires 1 in a step of the withdrawal process, is facilitated by the mechanical strength of the improved connection. This helps assure that electrode withdrawal will be uneventful and successful.

Strip electrodes 10 having eight or fewer sets of disks 11 and wires 19 which are made of metal of the aforementioned types are essentially unaffected by the use of magnetic resonance imaging (MRI) diagnostic techniques and equipment. That is, they are not magnetically attracted (or at least not significantly so) and therefore, exhibit no tendency to shift position when scanned by MRI machines of moderate power. Such machines are those having a maximum power of 1.5 Teslas or less and constitutes the maximum size of machines which are most commonly found in hospitals.

In addition, the exact position of strip and grid electrodes 10 of the type described above is readily ascertained using MRI equipment since the images of the disks 11 and wires 19 stand out very clearly. When subjected to X-rays for position determination, the images of such disks 11 and wires 19 tend to be obscured or "fuzzy," due in large part to their very low metallic mass.

While the principles of this invention have been described in connection with specific embodiments, it should be understood clearly that these descriptions are made only by way of example and are not intended to limit the scope of the invention.

What is claimed is:

1. An improved electrode for determining epileptogenic foci, such electrode being of the type having two dielectric layers, the electrode including:
   at least one electrical lead wire having at least a portion of its length interposed between the dielectric layers;
   at least one electrode disk interposed between the dielectric layers, such disk having a tab formed thereon and connected to the electrical lead wire, connection of such tab to such lead wire being by wrapping the wire on the tab and crimping the tab to the wire to create an electrically conductive circuit therebetween.

2. The electrode of claim 1 wherein the tab has an inward segment attached to and extending from the disk and an outer segment attached to and extending from the inward segment and the tab is crimped to the wire by folding the outer segment toward the inward segment and clamping the wire between such segments.

3. The electrode of claim 2 wherein the tab has a longitudinal axis and wherein the maximum dimension of the disk as measured generally normal to such longitudinal axis is at least four times greater than the width of the tab as measured normal to such longitudinal axis.

4. An improved subdural electrode for placement in contact with brain tissue to determine epileptogenic foci, such electrode being of the type having two dielectric layers, the electrode including:
   a plurality of electrode disks interposed between the dielectric layers, each of such disks being formed of an electrically conductive material and having a tab formed thereon for connection to an electrical lead wire, each such tab having a longitudinal axis;
   a separate electrical lead wire connected to each tab, each such lead wire having an insulated portion interposed between the dielectric layers and a bare portion, connection of each such tab to a bare portion of a lead wire being by placing such bare portion generally normal to such axis and crimping the tab to the wire to create an electrically conductive circuit therebetween.

5. The electrode of claim 4 wherein the tab has an inward segment and an outer segment and the tab is crimped to the wire by folding the outer segment toward the inward segment, thereby defining a fold so that the bare portion is clamped between the segments at a location immediately adjacent the fold.

6. The electrode of claim 5 wherein the bare portion of the lead wire is wrapped about the tab at least once and the tab is crimped to the wire by folding the outer segment toward the inward segment, thereby defining a fold and the bare portion is clamped between the segments at a location immediately adjacent the fold, thereby providing a more secure connection of the tab and the lead wire to one another.

7. The electrode of claim 6 wherein the bare portion of the lead wire is wrapped about the tab at least three times, thereby providing a more secure connection of the tab and the lead wire and further providing an increased area of electrical contact between the tab and the lead wire.

8. An improved electrode for determining epileptogenic foci, such electrode being of the type intended for placement between the brain and the dura tissue covering the brain, such electrode having a lower dielectric layer with a lower surface to be in contact with the brain and an imperforate upper dielectric layer to be in contact with the dura tissue, such lower dielectric layer having a plurality of openings therethrough for exposing an electrode disk at each opening, a plurality of electrode disks interposed and confined between the layers, each such disk being exposed through a separate opening in the lower dielectric layer and being connected to a separate electrical lead wire, each lead wire having an insulated portion and a bare portion, the improvement wherein:
   each disk includes a tab extending therefrom, each such tab having an inward segment and an outer segment;
   the bare portion of an electrical lead wire being wrapped about the tab, the outer segment being folded toward the inward segment to clamp the bare portion therebetween, the direction of folding of the outer segment being such that the outer segment lies adjacent the upper dielectric layer;
   whereby secure mechanical and electrical connection of the tab and the bare portion is effected and whereby the brain-contacting lower surface of the lower dielectric layer is made relatively smooth.

9. The electrode of claim 8 wherein the bare portion includes an exposed end and wherein such exposed end is positioned atop the disk adjacent the upper dielectric layer, thereby aiding in confining the exposed end within the upper dielectric layer.

10. The electrode of claim 8 wherein the tab and the disk are connected at a juncture and wherein the tab is folded toward the disk at the juncture to bring the tab into contact with the disk, the integrity of the mechanical and electrical connection between the lead wire and its disk thereby being improved.

11. The electrode of claim 8 wherein the bare portion of the electrical lead wire includes an end and wherein such end is confined between the outer segment and the inward segment.

12. The electrode of claim 8 wherein the bare portion of the electrical lead wire includes an end and wherein such end is positioned atop its associated disk and is confined by the upper dielectric layer.

13. The electrode of claim 8 wherein each tab has a longitudinal axis and wherein the maximum dimension of each disk as measured generally normal to such longitudinal axis is at least four times greater than the maximum dimension of its tab as measured normal to such longitudinal axis.

14. The electrode of claim 8 wherein the electrode is made of a material selected from a group of materials including platinum, nonferrous metal and stainless steel containing less than about 30% ferrous material, the position of the electrode within the cranium thereby being substantially unaffected by magnetic resonance imaging (MRI) techniques which use MRI machines of moderate power.

15. An improved subdural electrode for determining epileptogenic foci, such electrode being of the type having two dielectric layers, the electrode including:
   at least one electrical lead wire having at least a portion of its length interposed between the dielectric layers;;
   at least one electrode disk interposed between the dielectric layers, such disk having a tab formed thereon, such tab having an inward segment attached to and extending from the disk and an outer segment attached to and extending from the inward segment;
   such tab being connected to such lead wire by folding the outer segment toward the inward segment and clamping the wire between such segments to create an electrically conductive circuit therebetween.

16. An improved subdural electrode for determining epileptogenic foci, such electrode being of the type having two dielectric layers, the electrode including:
   at least one electrical lead wire having at least a portion of its length interposed between the dielectric layers, such wire having a bare portion;
   at least one electrode disk interposed between the dielectric layers, such disk having a tab attached thereto and connected to such bare portion, such tab having a longitudinal axis;
   connection of such tab to such bare portion being by placing such bare portion generally normal to such axis and crimping the tab to such bare portion to create an electrically conductive connection.

17. An improved subdural electrode for determining epileptogenic foci, such electrode being of the type having two dielectric layers, the electrode including:
- a plurality of electrode disks interposed between the dielectric layers, each of such disks being formed of an electrically conductive material and having a tab formed thereon for connection to an electrical lead wire, each such tab having an inward segment and an outer segment;
- a separate electrical lead wire connected to each disk, each such lead wire having an insulated portion interposed between the dielectric layers and a bare portion connected to the tab of a disk, connection of such tab to a bare portion being of folding the outer segment toward the inward segment, thereby defining a fold so that such bare portion is clamped between the segments at a location immediately adjacent the fold to create an electrically conductive connection therebetween.

18. The electrode of claim 17 wherein the lead wire is wrapped about the tab at least once.

19. The electrode of claim 18 wherein the bare portion of the lead wire is wrapped about the tab at least three times, thereby providing a more secure connection of the tab and the lead wire and further providing an increased area of electrical contact between the tab and the lead wire.

* * * * *

UNITED STATES PATENT AND TRADEMARK OFFICE
CERTIFICATE OF CORRECTION

PATENT NO. : 5,097,835
DATED : March 24, 1992
INVENTOR(S) : David A. Putz It is certified that error appears in the above-identified patent and that said Letters Patent is hereby corrected as shown below:

In column 1, line 43, delete "rain" and insert --brain--.

In column 2, line 3, delete "Also" and insert --All--.

In column 2, line 5, delete "phychologically" and insert --psychologically--.

In column 4, line 53, delete "epileoptogenic" and insert --epileptogenic--.

In column 8, line 19, delete "detected" and insert --detect--.

In column 8, line 23, delete "1" and insert --19--.

In claim 1, line 1, after "improved" insert --subdural--.

Signed and Sealed this

Eighth Day of June, 1993

Attest:

MICHAEL K. KIRK

*Attesting Officer*    *Acting Commissioner of Patents and Trademarks*